(12) United States Patent
Wessels et al.

(10) Patent No.: US 11,992,705 B2
(45) Date of Patent: May 28, 2024

(54) ON-LINE ADAPTIVE DEEP INSPIRATION BREATH-HOLD TREATMENT

(71) Applicant: SIEMENS HEALTHINEERS INTERNATIONAL AG, Palo Alto, CA (US)

(72) Inventors: Carsten Wessels, Baden Dättwil (CH); Ekta Jhala, Steinhausen (CH); Anke Engbert, Baden Dättwil (CH)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 162 days.

(21) Appl. No.: 17/488,878

(22) Filed: Sep. 29, 2021

(65) Prior Publication Data
US 2023/0097277 A1    Mar. 30, 2023

(51) Int. Cl.
*A61N 5/10* (2006.01)

(52) U.S. Cl.
CPC .......... *A61N 5/1037* (2013.01); *A61N 5/103* (2013.01); *A61N 5/1031* (2013.01); *A61N 5/1042* (2013.01); *A61N 5/1049* (2013.01); *A61N 5/1067* (2013.01); *A61N 5/1069* (2013.01); *A61N 5/1081* (2013.01); *A61N 2005/1051* (2013.01); *A61N 2005/1054* (2013.01);
(Continued)

(58) Field of Classification Search
CPC ........ A61N 5/10; A61N 5/103; A61N 5/1031; A61N 5/1037; A61N 5/1042; A61N 5/1048; A61N 5/1049; A61N 2005/1051; A61N 2005/1054; A61N 2005/1059; A61N 2005/1061; A61N 5/1064; A61N 5/1065; A61N 5/1067; A61N 5/1069; A61N 5/107; A61N 2005/1074; A61N 5/1077; A61N 5/1081
USPC .......................................................... 378/65
See application file for complete search history.

(56) References Cited

U.S. PATENT DOCUMENTS

| 7,260,426 B2* | 8/2007 | Schweikard | A61B 34/20 600/595 |
| 7,352,370 B2* | 4/2008 | Wang | A61N 5/103 382/154 |

(Continued)

FOREIGN PATENT DOCUMENTS

EP    3456383 A1    3/2019

OTHER PUBLICATIONS

The Extended European Search Report, application No. 22197167.4, dated Feb. 23, 2023.
(Continued)

*Primary Examiner* — Allen C. Ho
(74) *Attorney, Agent, or Firm* — SU IP CONSULTING

(57) ABSTRACT

A computer-implemented method of performing a radiation therapy process includes: while a patient is disposed in a first position and maintains a first inspiration level, acquiring a set of projection images of a target volume associated with the patient; based on a treatment planning digital volume associated with the radiation therapy process and the set of projection images, generating a synthetic digital volume that includes the target volume; based on a treatment plan associated with the treatment planning digital volume and on the synthetic digital volume, generating a modified treatment fraction; and while the patient remains in the first position and maintains at least the first inspiration level, performing the modified treatment fraction.

20 Claims, 10 Drawing Sheets

(52) U.S. Cl.
CPC .............. *A61N 2005/1059* (2013.01); *A61N 2005/1061* (2013.01)

(56) References Cited

U.S. PATENT DOCUMENTS

| | | | | |
|---|---|---|---|---|
| 7,453,983 B2* | 11/2008 | Schildkraut | .......... | A61N 5/1049 378/65 |
| 7,453,984 B2* | 11/2008 | Chen | .......... | A61N 5/1049 378/92 |
| 7,505,559 B2* | 3/2009 | Kuduvalli | .......... | A61N 5/1049 378/65 |
| 7,522,779 B2* | 4/2009 | Fu | .......... | G06T 7/35 382/167 |
| 7,551,717 B2* | 6/2009 | Tome | .......... | A61B 5/6831 378/65 |
| 7,570,738 B2* | 8/2009 | Khamene | .......... | A61B 6/032 378/65 |
| 7,609,810 B2* | 10/2009 | Yi | .......... | A61N 5/1049 378/65 |
| 7,623,679 B2* | 11/2009 | West | .......... | G06V 10/255 382/128 |
| 7,713,205 B2* | 5/2010 | Fu | .......... | A61N 5/1049 600/443 |
| 7,715,606 B2* | 5/2010 | Jeung | .......... | A61B 90/36 378/65 |
| 7,720,196 B2* | 5/2010 | Zhang | .......... | A61B 6/4458 378/65 |
| 7,835,493 B2* | 11/2010 | Keall | .......... | A61N 5/1042 378/65 |
| 7,853,308 B2* | 12/2010 | Sauer | .......... | A61N 5/1049 378/65 |
| 7,894,649 B2* | 2/2011 | Fu | .......... | A61N 5/1049 378/65 |
| 7,935,939 B2* | 5/2011 | Aoi | .......... | A61N 5/1049 250/493.1 |
| 8,042,209 B2* | 10/2011 | D'Souza | .......... | A61N 5/1049 5/610 |
| 8,229,068 B2* | 7/2012 | Lu | .......... | A61N 5/1049 378/65 |
| 8,358,738 B2* | 1/2013 | Brown | .......... | A61N 5/1037 378/65 |
| 10,279,196 B2* | 5/2019 | West | .......... | A61N 5/1031 |
| 10,342,996 B2* | 7/2019 | Jordan | .......... | A61N 5/1049 |
| 10,532,224 B2* | 1/2020 | Jordan | .......... | A61N 5/1039 |
| 10,737,117 B2* | 8/2020 | Mori | .......... | A61N 5/1065 |
| 10,769,467 B2* | 9/2020 | Hirai | .......... | G06V 20/647 |
| 10,835,762 B2* | 11/2020 | Mori | .......... | A61N 5/1067 |
| 10,872,427 B2* | 12/2020 | Berlinger | .......... | A61N 5/1037 |
| 10,940,331 B2* | 3/2021 | Mori | .......... | A61N 5/1064 |
| 10,952,695 B2* | 3/2021 | Mori | .......... | A61B 6/487 |
| 10,967,202 B2* | 4/2021 | Van Heteren | .......... | A61N 5/1081 |
| 11,027,153 B2* | 6/2021 | Van Heteren | .......... | A61N 5/1081 |
| 11,141,126 B2* | 10/2021 | Mori | .......... | G06T 7/20 |
| 11,154,269 B2* | 10/2021 | Shea | .......... | A61N 5/1081 |
| 11,278,743 B1* | 3/2022 | Frederick | .......... | G06V 10/25 |
| 11,295,449 B2* | 4/2022 | Feain | .......... | A61B 6/032 |
| 11,433,257 B2* | 9/2022 | Givehchi | .......... | A61N 5/1049 |
| 11,443,441 B2* | 9/2022 | Berlinger | .......... | A61N 5/1049 |
| 11,446,520 B2* | 9/2022 | Fujii | .......... | A61N 5/1048 |
| 11,478,660 B2* | 10/2022 | Nord | .......... | G06T 7/0012 |
| 11,478,662 B2* | 10/2022 | Sayeh | .......... | G16H 40/63 |
| 11,504,550 B2* | 11/2022 | Maolinbay | .......... | A61B 6/4085 |
| 11,647,975 B2* | 5/2023 | La Riviere | .......... | A61B 6/5205 378/62 |
| 11,679,276 B2* | 6/2023 | Novosad | .......... | A61N 5/1067 378/65 |
| 11,684,801 B2* | 6/2023 | Schadewaldt | .......... | A61N 5/1037 600/1 |
| 11,759,658 B2* | 9/2023 | Strzelecki | .......... | G06T 5/77 378/62 |
| 11,794,039 B2* | 10/2023 | Bai | .......... | A61B 6/5258 |
| 2019/0366124 A1 | 12/2019 | Berlinger | | |

OTHER PUBLICATIONS

Jones K et al., "PO-1972 DIBH for mediastinal lymphoma: Implementation and evaluation of a 5-year service", Radiotherapy and Oncology, Elsevier, Aug. 1, 2021, vol. 161.

* cited by examiner

ON-LINE ADAPTIVE DEEP INSPIRATION BREATH-HOLD TREATMENT

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. From such imaging, the size and mass of the target tissue can be estimated and an appropriate treatment plan generated and planning target volume determined.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues prior to or while radiation treatment is delivered to the planning target volume. IGRT incorporates imaging coordinates from the treatment plan to ensure the patient is properly aligned for treatment in the radiation therapy device.

SUMMARY

In accordance with at least some embodiments of the present disclosure, a method of breath-hold-based radiation therapy is disclosed in which a modified treatment fraction is generated and implemented when a patient is unable to maintain a threshold inspiration level on which a treatment plan is based. Specifically, prior to performing each treatment fraction of a treatment plan, the breathing capabilities of the patient are determined. When the patient is unable to maintain a breath-hold level that is equal to or greater than the threshold inspiration level, patient anatomy is imaged at an achievable inspiration level and a modified treatment fraction is generated based on the original treatment plan and the images of the patient anatomy at the achievable inspiration level. The modified treatment fraction is then performed while the patient maintains a breath-hold level that is equal to or greater than the achievable inspiration level. Thus, each treatment fraction can be adapted to the breathing capabilities of the patient at the time the treatment fraction is performed. As a result, even patients who cannot maintain the threshold inspiration level on which a treatment plan is based can benefit from deep-inspiration breath-hold treatments.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
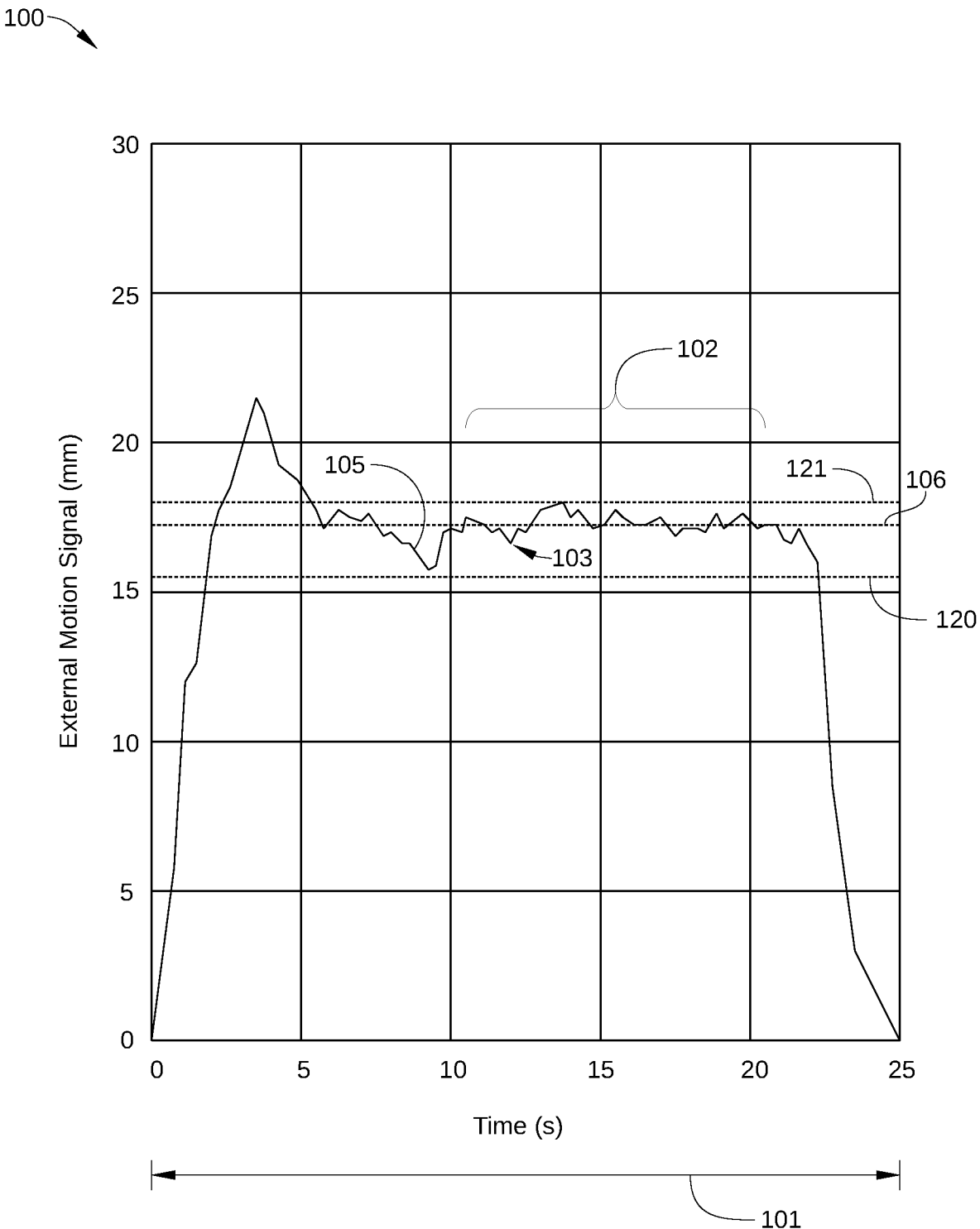
FIG. 1 is an illustration of a breath-hold curve associated with a treatment planning process, according to various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Introduction

Image guided radiation therapy (IGRT) is used to treat tumors in areas of the body that are subject to voluntary movement, such as the lungs, or involuntary movement, such as organs affected by peristalsis, gas motion, muscle contraction and the like. IGRT involves the use of an imaging system to view target tissues (also referred to as the "target volume") prior to or while radiation treatment is delivered thereto. In IGRT, image-based coordinates of the target volume from a previously determined treatment plan are compared to image-based coordinates of the target volume determined during the application of the treatment beam. In this way, changes in the surrounding organs at risk and/or motion or deformation of the target volume relative to the radiation therapy system can be detected. Consequently, dose limits to organs at risk are accurately enforced based on the daily position and shape, and the patient's position and/or the treatment beam can be adjusted to more precisely target the radiation dose to the tumor. For example, in pancreatic tumor treatments, organs at risk include the duodenum and stomach. The shape and relative position of these organs at risk with respect to the target volume can vary significantly from day-to-day. Thus, accurate adaption to the shape and relative position of such organs at risk enables escalation of the dose to the target volume and better therapeutic results.

In some radiation therapy systems, breath-hold-based radiation therapy is performed, such as deep-inspiration breath hold (DIBH) treatment, in which the patient performs one or more breath holds throughout a particular treatment fraction. DIBH treatment is often employed to separate an organ at risk or other critical anatomical structures from the target volume during the treatment fraction. In addition, DIBH treatment can reduce the motion and/or deformation of a target volume caused by patient respiration, thereby reducing the dose received by non-target tissue.

One drawback to DIBH treatment is that the patient cannot receive a treatment fraction unless able to perform a breath-hold at the same inspiration level that was achieved during the initial acquisition of the planning computed tomography scan. If the patient is unable to perform such a breath-hold at the time of treatment, a free-breathing plan is delivered instead. Generally, a free-breathing plan delivers more dose to the organs at risk (such as the heart in the case of breast cancer radiation therapy) and can have increased short- and long-term treatment side effects for the patient.

Patient Breathing Signal

According to various embodiments, a modified treatment fraction is generated and implemented when a patient is unable to maintain a threshold inspiration level on which a treatment plan for that patient is based. In some embodiments, the ability for the patient to maintain a particular inspiration level is based on a breathing signal that indicates a current inspiration level of the patient. In such embodiments, the breathing signal can be measured using a fiducial, a marker block or other internal or external marker, and/or a surface recognition system that detects motion of a surface the patient's body. In some embodiments, the breathing signal of a patient can be represented as a breath-hold curve that indicates the patient inspiration level over time. Embodiments of different breath-hold curves are described below in conjunction with FIGS. 1 and 2.

FIG. 1 is an illustration of a breath-hold curve 100 associated with a treatment planning process, according to various embodiments. Breath-hold curve 100 shows variations in a motion signal 105 over a time interval 101 that includes a patient breath hold. In the embodiment illustrated in FIG. 1, time interval 101 is associated with a patient breath hold performed during a planning CT scan of patient anatomy and/or during a training session prior to the planning CT scan. Generally, the planning CT scan of the patient involves the acquisition of a set of projection images of the patient anatomy that includes a target volume, such as a tumor. To facilitate DIBH treatment, the patient typically performs a maximum or near-maximum inspiration of breath during the planning CT scan, so that the target volume is separated from organs at risk or other critical anatomical structures during subsequent treatment fractions. Thus, motion signal 105 is associated with a maximum or near-maximum inspiration of breath by the patient during time interval 101.

In some embodiments, the specific value of motion signal 105 that is associated with breath-hold curve 100 is determined based at least in part on a motion trace of a point or points on the surface of the body of the patient and/or one or more internal or external markers (e.g., fiducials, surface markers, and the like). For example, in some embodiments, the measurement of motion signal 105 is performed via patient-monitoring optical sensors associated with the system performing the planning CT scan and one or more fiducials, other markers, position sensors, and/or detected locations on the surface of the body of the patient. Generally, the location of the fiducials, markers, position sensors, and/or detected locations on the surface of the body are selected so that said fiducials, markers, position sensors, and/or detected locations move synchronously, or substantially synchronously, with the target volume of the patient. Thus, in such embodiments, motion associated with the respiration cycle of the patient is accurately measured over time interval 101. Such motion may be measured relative to any suitable datum location within or proximate to the anatomy of the patient.

In some embodiments, the value of motion signal 105 at each point in time in breath-hold curve 100 is based on the detected motion of a single internal or external marker, fiducial, or point on the surface of the body of the patient. In other embodiments, the value of motion signal 105 at each point in time in breath-hold curve 100 is based on the detected motion of multiple internal or external markers, fiducials, and/or points on the surface of the body of the patient. In such embodiments, the values of motion signal 105 may be based on an average of multiple motion values, where each motion value is associated with a different internal or external marker, fiducial, and/or point on the surface of the body of the patient. In such embodiments, the average of the multiple motion values can be a weighted average or a simple average.

In DIBH therapy, a predetermined threshold level 120 is determined for the patient, based on motion signal 105. Predetermined threshold level 120 indicates a minimum allowable inspiration level to be maintained by the patient during the performance of a DIBH treatment fraction that separates an organ at risk or other critical anatomical structures from the target volume during the treatment fraction. In DIBH therapy, a treatment plan for the patient is generated in a planning treatment process that is based on the patient maintaining an inspiration level that is equal to or greater than predetermined threshold level 120 during a treatment fraction. Thus, when the patient cannot maintain an inspiration level equal to or greater than predetermined threshold level 120, allowable movement of patient anatomy relative to the target volume may be exceeded, and the treatment plan cannot be safely performed without modification.

In the embodiment illustrated in FIG. 1, predetermined threshold level 120 is expressed as an absolute displacement distance that is associated with breath-hold curve 100, for example, 1.7 millimeters less than (and/or greater than) characteristic inspiration level 106. In such embodiments, characteristic inspiration level 106 is also expressed as an absolute displacement distance associated with breath-hold curve 100, for example, 17.3 mm. Alternatively, in some embodiments, predetermined threshold level 120 may be expressed as a percentage of a characteristic inspiration level 106 that is associated with breath-hold curve 100, for example, 90% of characteristic inspiration level 106.

In some embodiments, characteristic inspiration level 106 is based on an average inspiration level achieved during a time interval 102 that is associated with motion signal 105. In the embodiment illustrated in FIG. 1, time interval 102 corresponds to a time during which the detected patient inspiration level remains substantially constant. In other embodiments, time interval 102 corresponds to most or all of time interval 101, or some other time interval associated with breath-hold curve 100, such as a final portion of time interval 101, a middle portion of time interval 101, etc. In some embodiments, characteristic inspiration level 106 is based on a lowest inspiration level 103 achieved during time interval 102.

In some embodiments, in DIBH therapy, multiple predetermined threshold levels based on motion signal 105 are determined for the patient, such as a minimum threshold level and a maximum threshold level. In the embodiment illustrated in FIG. 1, predetermined threshold level 120 is implemented as the minimum threshold level based on motion signal 105, and predetermined threshold level 121 is implemented as the maximum threshold level based on motion signal 105. In the embodiment, predetermined threshold level 121 is determined based on a percentage of characteristic inspiration level 106 that is associated with breath-hold curve 100, for example, 105% of characteristic inspiration level 106, or 18.1 mm. In such embodiments, a treatment plan for the patient is generated in a planning treatment process that is based on the patient maintaining an inspiration level that is equal to or greater than predetermined threshold level 120 and equal to or less than predetermined threshold level 121 during a treatment fraction.

Figure 2:
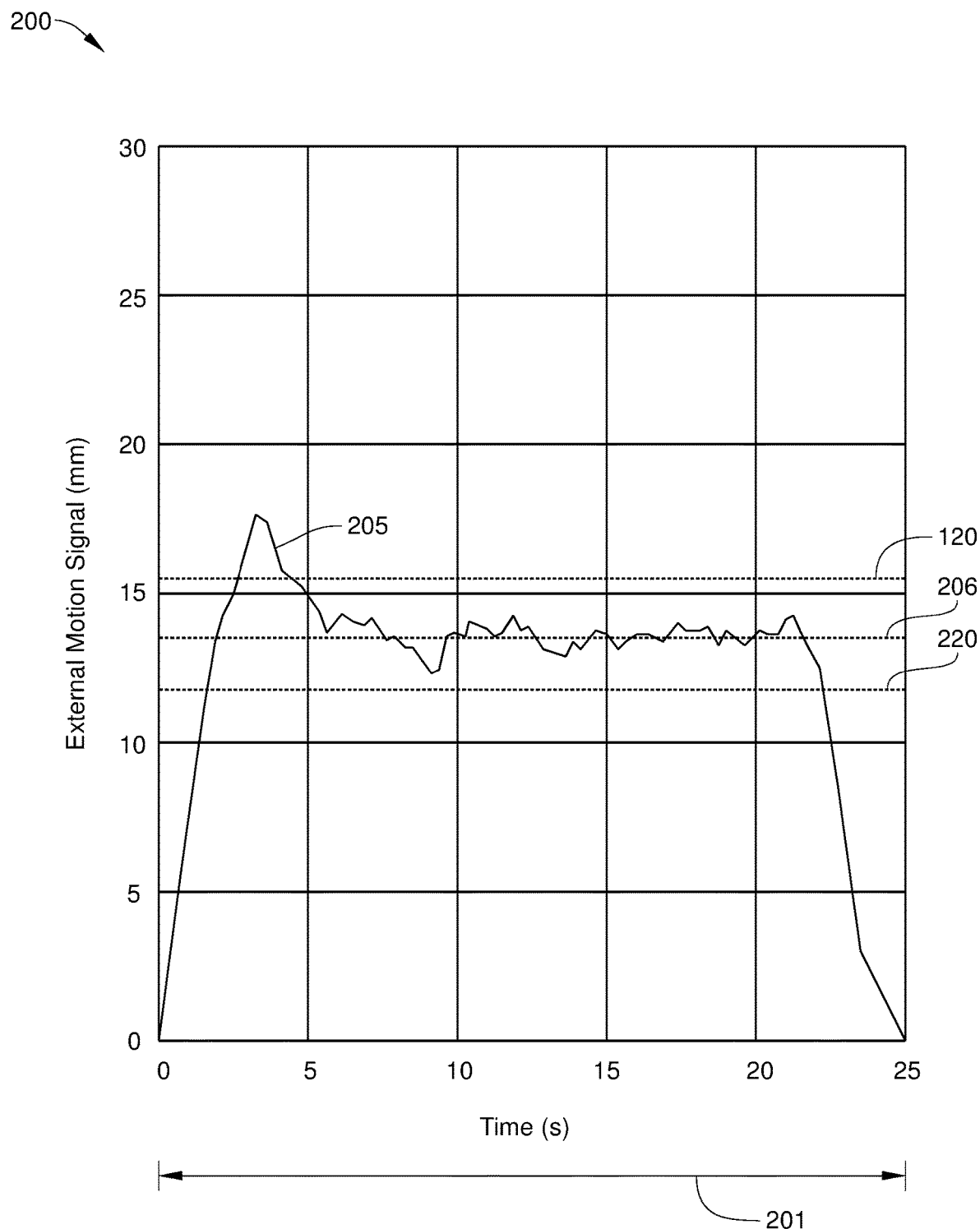
FIG. 2 is an illustration of a breath-hold curve associated with a treatment fraction of a treatment plan, according to various embodiments.

FIG. 2 is an illustration of a breath-hold curve 200 associated with a treatment fraction of a treatment plan, according to various embodiments. Breath-hold curve 200 shows variations in a motion signal 205 over a time interval 201 that includes a patient breath hold. In the embodiment illustrated in FIG. 2, time interval 201 is associated with a patient breath hold performed in preparation for a treatment fraction to be performed, such as during patient setup for a particular treatment fraction. As such, the patient breath hold associated with breath-hold curve 200 is performed immediately prior to treatment, for example after the patient has been positioned on a radiation therapy system couch for treatment and before the treatment fraction has begun to be performed.

Similar to motion signal 105 in FIG. 1, motion signal 205 is determined based at least in part on a motion trace of a point or points on the surface of the body of the patient and/or one or more internal or external markers (e.g., fiducials, surface markers, and the like). For reference, predetermined threshold level 120 for the patient is also shown in FIG. 2. According to various embodiments, based on motion signal 205, a modified treatment fraction may be generated and implemented while the patient remains positioned on the radiation therapy system couch for treatment. Specifically, when motion signal 205 indicates that the patient cannot maintain a suitable inspiration level (for example, an inspiration level greater than or equal to predetermined threshold level 120), a current fraction inspiration threshold 220 is determined based on motion signal 205. For example, current fraction inspiration threshold 220 can be determined based on motion signal 205 and characteristic inspiration level 206 in the same way that predetermined threshold level 120 is based on motion signal 105. The modified treatment fraction is then generated and implemented, as described below in conjunction with FIGS. 7 and 8.

System Overview

Figure 3:
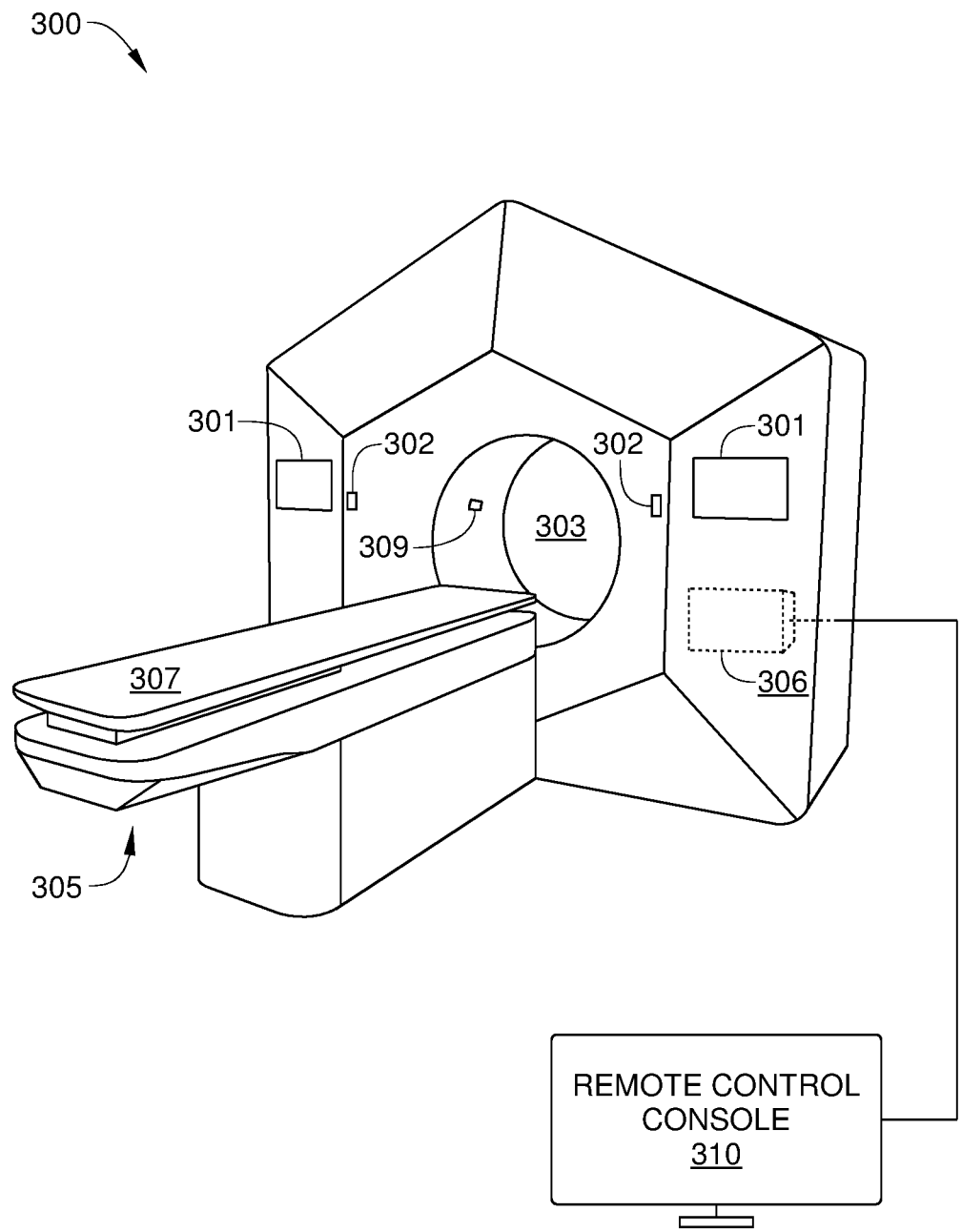
FIG. 3 is a perspective view of a radiation therapy system that can beneficially implement various aspects of the present disclosure.

FIG. 3 is a perspective view of a radiation therapy system 300 that can beneficially implement various aspects of the present disclosure. Radiation therapy (RT) system 300 is a radiation system configured to detect intra-fraction motion in near-real time using X-ray imaging techniques. Thus, RT system 300 is configured to provide stereotactic radiosurgery and precision radiotherapy for lesions, tumors, and conditions anywhere in the body where radiation treatment is indicated. As such, RT system 300 can include one or more of a linear accelerator (LINAC) that generates a megavolt (MV) treatment beam of high energy X-rays, a kilovolt (kV) X-ray source, one or more X-ray imagers, and, in some embodiments, an MV electronic portal imaging device (EPID). By way of example, RT system 300 is described herein configured with a circular gantry. In other embodiments, RT system 300 can be configured with a C-gantry capable of infinite rotation via a slip ring connection.

Generally, RT system 300 is capable of kV imaging of a target volume during application of an MV treatment beam, so that an IGRT and/or an intensity-modulated radiation therapy (IMRT) process can be performed using X-ray imaging. RT system 300 may include one or more touchscreens 301, couch motion controls 302, a bore 303, a base positioning assembly 305, a couch 307 disposed on base positioning assembly 305, and an image acquisition and treatment control computer 306, all of which are disposed within a treatment room. RT system 300 further includes a remote control console 310, which is disposed outside the treatment room and enables treatment delivery and patient monitoring from a remote location. Exemplary embodiments of a computing device that can be implemented as image acquisition and treatment control computer 306 and/ or remote control console 310 is described below in conjunction with FIG. 9. Base positioning assembly 305 is configured to precisely position couch 307 with respect to bore 303, and couch motion controls 302 include input devices, such as button and/or switches, that enable a user to operate base positioning assembly 305 to automatically and precisely position couch 307 to a predetermined location with respect to bore 303. Couch motion controls 302 also enable a user to manually position couch 307 to a predetermined location.

In some embodiments, RT system 300 further includes one or more patient-monitoring optical sensors 309. Patient-monitoring optical sensors 309 are configured as a patient position-monitoring system that generates an external motion signal indicating a specific magnitude of respiratory motion by a patient on couch 307. Thus, patient-monitoring sensors 309 can obtain a motion trace of one or more points on a surface of the body of the patients, for example based on the motion of a fiducial or other internal or external marker (or markers) or location(s) on the surface of the patient that is/are positioned to move synchronously with a target volume of the patient. In some embodiments, patient-monitoring optical sensors 309 include one or more cameras, surface scanners, and/or the like.

Figure 4:
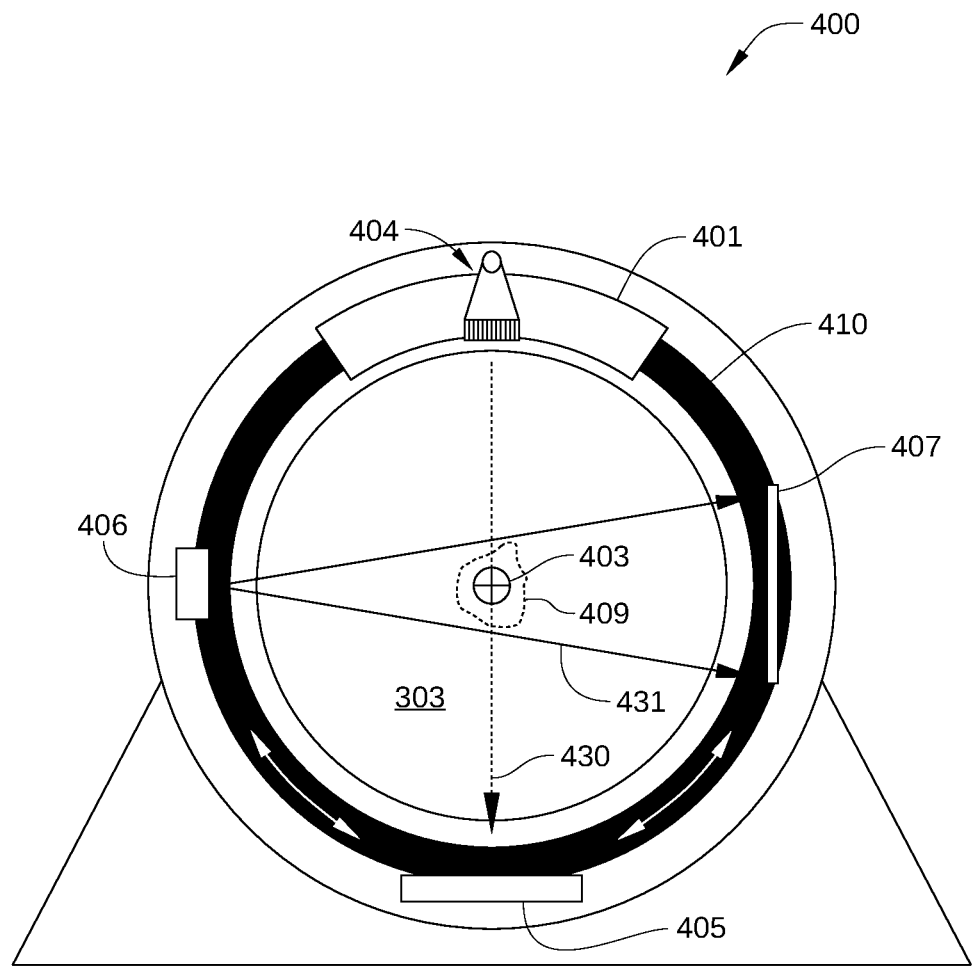
FIG. 4 schematically illustrates a drive stand and gantry of the radiation therapy system of FIG. 1, according to various embodiments.

FIG. 4 schematically illustrates a drive stand 400 and gantry 410 of RT system 300, according to various embodiments. Covers, base positioning assembly 305, couch 307, and other components of RT system 300 are omitted in FIG. 4 for clarity. Drive stand 400 is a fixed support structure for components of RT treatment system 310, including gantry 410 and a drive system 401 for rotatably moving gantry 410. Drive stand 400 rests on and/or is fixed to a support surface that is external to RT treatment system 310, such as a floor of an RT treatment facility. Gantry 410 is rotationally coupled to drive stand 400 and is a support structure on which various components of RT system 300 are mounted, including a linear accelerator (LINAC) 404, an MV electronic portal imaging device (EPID) 405, an imaging X-ray source 406, and an X-ray imager 407. During operation of RT treatment system 310, gantry 420 rotates about bore 303 when actuated by drive system 401.

Drive system 401 rotationally actuates gantry 410. In some embodiments, drive system 401 includes a linear motor that can be fixed to drive stand 400 and interacts with a magnetic track (not shown) mounted on gantry 410. In other embodiments, drive system 401 includes another suitable drive mechanism for precisely rotating gantry 410 about bore 303. LINAC 404 generates an MV treatment beam 430 of high energy X-rays (or in some embodiments electrons, protons, and/or other heavy charged particles, ultra-high dose rate X-rays (e.g., for FLASH radiotherapy) or microbeams for microbeam radiation therapy) and EPID 405 is configured to acquire X-ray images with treatment beam 430. Imaging X-ray source 406 is configured to direct a conical beam of X-rays, referred to herein as imaging X-rays 431, through an isocenter 403 of RT system 300 to X-ray imager 407, and isocenter 403 typically corresponds to the location of a target volume 409 to be treated. In the embodiment illustrated in FIG. 4, X-ray imager 407 is depicted as a planar device, whereas in other embodiments, X-ray imager 407 can have a curved configuration.

X-ray imager 407 receives imaging X-rays 431 and generates suitable projection images therefrom. According to certain embodiments, such projection images can then be employed to construct or update portions of imaging data for a digital volume that corresponds to a three-dimensional (3D) region that includes target volume 409. That is, a 3D image of such a 3D region is reconstructed from the projection images. In some embodiments, cone-beam computed tomography (CBCT) and/or digital tomosynthesis (DTS) can be used to process the projection images generated by X-ray imager 407. CBCT is typically employed to acquire projection images over a relatively long acquisition arc, for example over a rotation of 180° or more of gantry 410. As a result, a high-quality 3D reconstruction of the imaged volume can be generated. CBCT is often employed at the beginning of a radiation therapy session to generate a set-up 3D reconstruction. For example, CBCT may be employed immediately prior to application of treatment beam 430 to generate a 3D reconstruction confirming that target volume 409 has not moved or changed shape. Alternatively or additionally, in some embodiments, partial-data reconstruction is performed by RT system 300 during portions of an IGRT or IMRT process in which partial image data is employed to generate a 3D reconstruction of target volume 409. For example, as treatment beam 430 is directed to isocenter 403 while gantry 410 rotates through a treatment arc, DTS image acquisitions can be performed to generate image data for target volume 409. Because DTS image acquisition is performed over a relatively short acquisition arc, for example between about 10° and 60°, near real-time feedback for the shape and position of target volume 409 can be provided by DTS imaging during the IGRT process.

In the embodiment illustrated in FIG. 4, RT system 300 includes a single X-ray imager and a single corresponding imaging X-ray source. In other embodiments, RT system 300 can include two or more X-ray imagers, each with a corresponding imaging X-ray source. One such embodiment is illustrated in FIG. 5.

Figure 5:
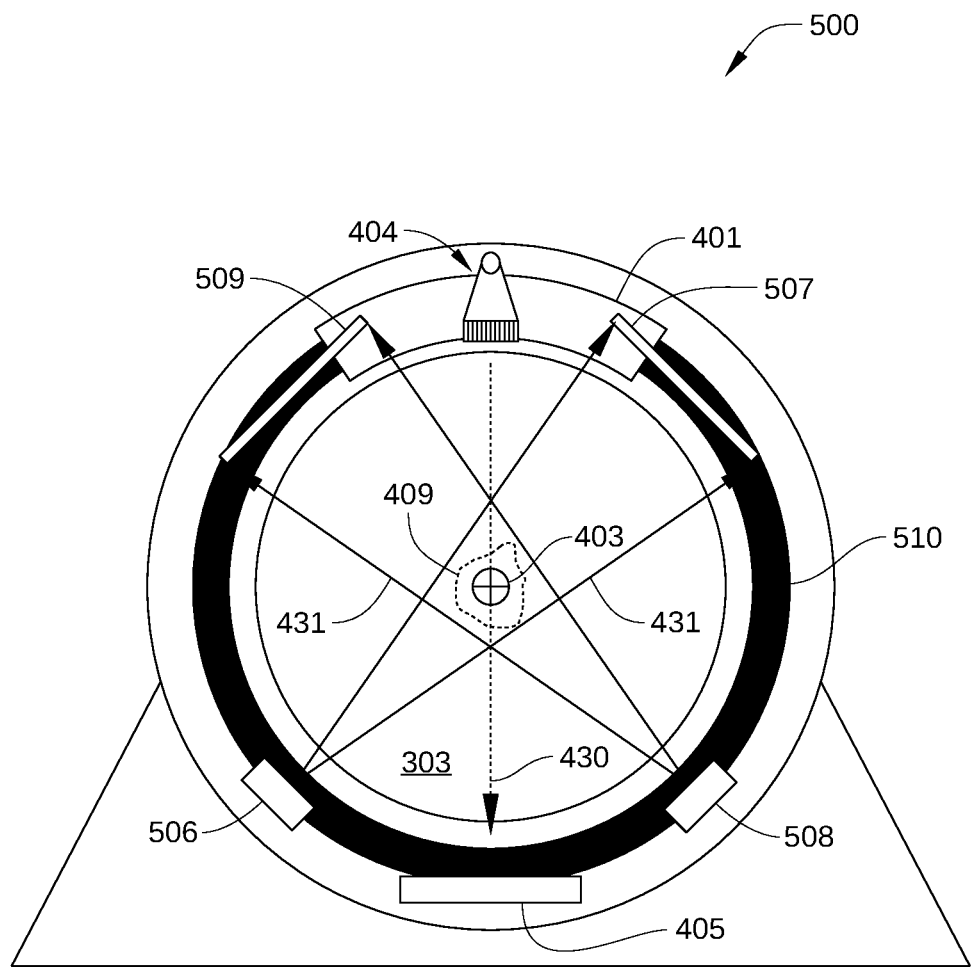
FIG. 5 schematically illustrates a drive stand and a gantry of the radiation therapy system of FIG. 1, according to various embodiments.

FIG. 5 schematically illustrates a drive stand 500 and gantry 510 of RT system 300, according to various embodiments. Drive stand 500 and gantry 510 are substantially similar in configuration to drive stand 400 and gantry 400 in FIG. 4, except that the components of RT system 300 that are mounted on gantry 510 include a first imaging X-ray source 506, a first X-ray imager 507, a second imaging X-ray source 508, and a second X-ray imager 509. In such embodiments, the inclusion of multiple X-ray imagers in RT system 300 facilitates the generation of projection images (for reconstructing the target volume) over a shorter image acquisition arc. For instance, when RT system 300 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 407 (or by first x-ray imager 507 and second X-ray imager 509) are used to construct imaging data for a digital volume of patient anatomy within a 3D region that includes the target volume. Alternatively or additionally, such projection images can be used to update portions of an existing imaging data for the digital volume corresponding to the 3D region. One embodiment of such a digital volume is described below in conjunction with FIG. 6.

Figure 6:
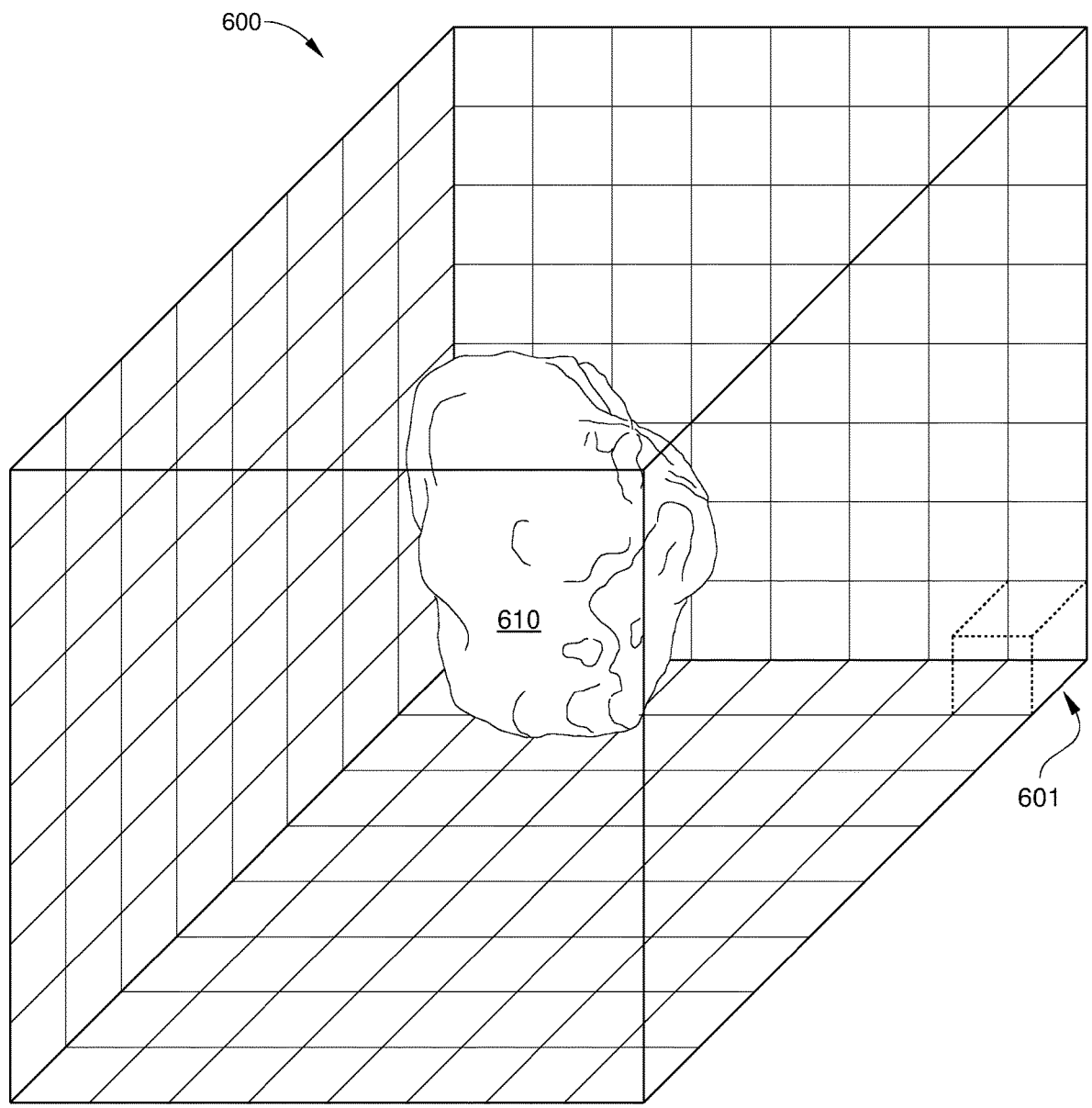
FIG. 6 schematically illustrates a digital volume that is constructed based on projection images generated by one or more X-ray imagers included in the radiation therapy system of FIG. 1, according to various embodiments.

FIG. 6 schematically illustrates a digital volume 600 that is constructed based on projection images generated by one or more X-ray imagers included in RT system 300, according to various embodiments. For example, in some embodiments, the projection images can be generated by a single X-ray imager, such as X-ray imager 407, and in other embodiments the projection images can be generated by multiple X-ray imagers, such as first x-ray imager 507 and second X-ray imager 509.

Digital volume 600 includes a plurality of voxels 601 (dashed lines) of anatomical image data, where each voxel 601 corresponds to a different location within digital volume 600. For clarity, only a single voxel 601 is shown in FIG. 6. Digital volume 600 corresponds to a 3D region that includes target volume 610. In FIG. 6, digital volume 600 is depicted as an 8×8×8 voxel cube, but in practice, digital volume 600 generally includes many more voxels, for example orders of magnitude more than are shown in FIG. 6.

For purposes of discussion, target volume 610 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 600.

In some embodiments, image information associated with each voxel 601 of digital volume 600 is constructed via projection images generated by single or multiple X-ray imagers via a CBCT process. For example, such a CBCT process can be employed immediately prior to delivering treatment beam 430 to target volume 610, so that the location and shape of target volume 610 can be confirmed before treatment begins. In addition, in some embodiments, image information associated with some or all of voxels 601 of digital volume 600 is updated via projection images generated by the single or multiple X-ray imagers. In this way, the location and shape of target volume 610 can be confirmed while the treatment is underway. Thus, if a sufficient portion of the target volume 610 is detected to be extending outside a threshold region, the treatment can either be aborted or modified.

Adaptive Deep-Inspiration Breath-Hold Treatment

According to various embodiments, a modified treatment fraction is generated and implemented when a patient is unable to maintain the threshold inspiration level on which a treatment plan for that patient is based. In some embodiments, the ability of the patient to maintain the threshold inspiration level is checked prior to beginning each treatment fraction of a treatment plan. In such embodiments, when the determination is made that the patient can maintain the threshold inspiration level, a normal treatment fraction is implemented, and when the determination is made that the patient cannot maintain the threshold inspiration level, a modified treatment fraction is generated and implemented. One such embodiment is described below in conjunction with FIG. 7.

Figure 7:
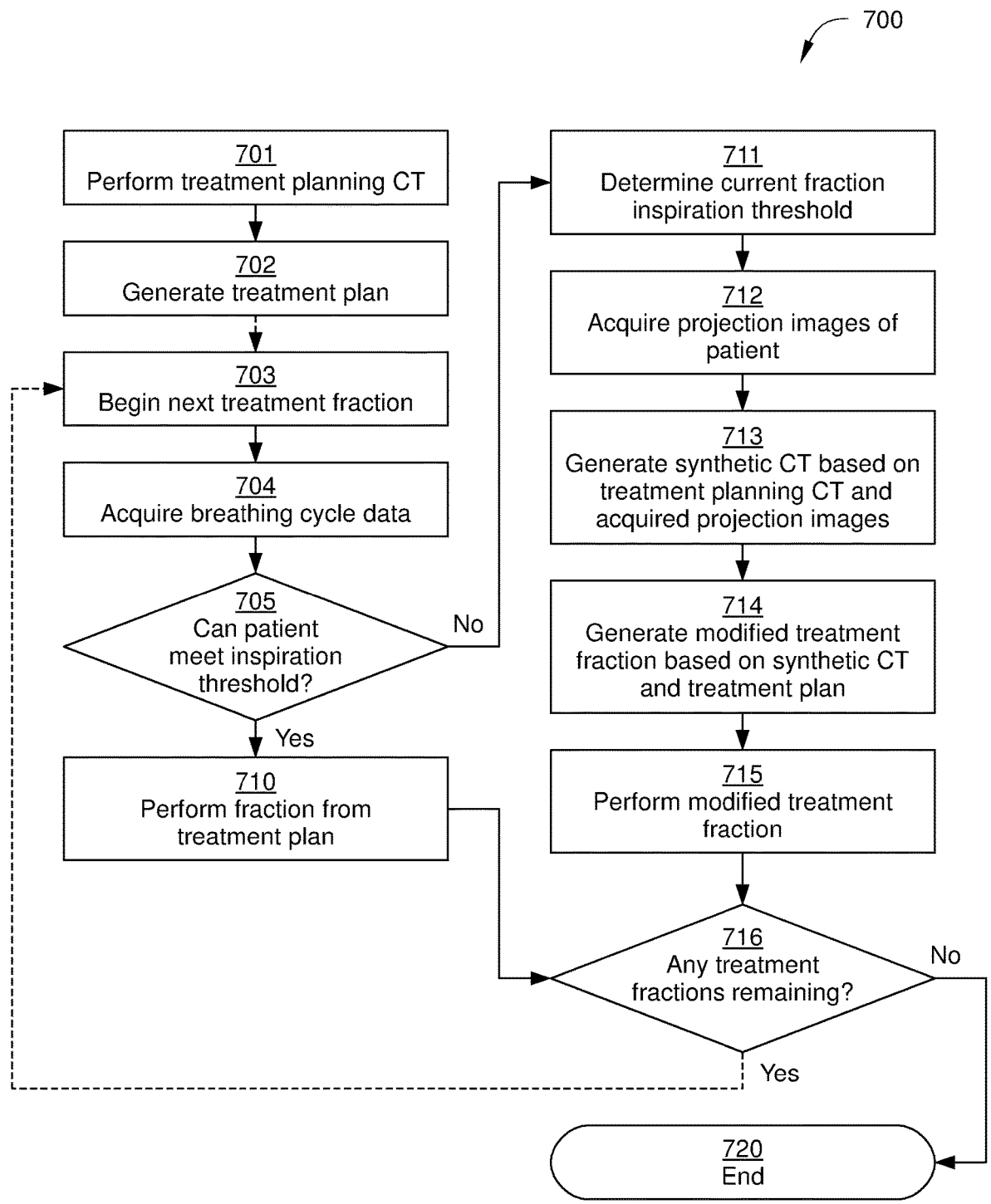
FIG. 7 sets forth a flowchart of a radiation therapy process, according to one or more embodiments.

FIG. 7 sets forth a flowchart of a radiation therapy process 700, according to one or more embodiments. Radiation therapy process 700 may include one or more operations, functions, or actions as illustrated by one or more of blocks 701-720. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although radiation therapy process 700 is described in conjunction with the systems of FIGS. 1-6, persons skilled in the art will understand that any suitably configured radiation therapy system is within the scope of the present embodiments.

Certain blocks 701-720 can be performed by a single computing device or by multiple computing devices. For example, in some embodiments, blocks 703-716 are performed by one or more computing devices associated with a radiation therapy system, such as image acquisition and treatment control computer 506 and/or remote control console 510 of FIG. 5. Further, in some embodiments certain blocks 701-720 can be performed by multiple systems. For example, in some embodiments, block 701 is performed by an imaging CT system, block 702 is performed by one or more treatment planning systems, and blocks 703-716 are performed by a radiation therapy system.

In step 701, a treatment planning CT scan is performed on a region of patient anatomy around a target volume (e.g., a tumor or other target tissue) and a 3D treatment planning CT image is generated. Generally, the treatment planning CT image is generated by scanning the patient (for example, acquiring a set of projection images of a target volume), such as during a clinical visit. The treatment planning CT image is a treatment planning digital volume that includes the target volume and is generated based on the projection images acquired in step 701. The treatment planning CT scan is performed while the patient maintains an inspiration level that is equal to or greater than predetermined threshold level 120. Any technically feasible CT scanning process can be employed to generate the treatment planning CT, such as spiral CT or CBCT.

In step 702, a treatment plan is generated for the patient. Generally, the process of generating the treatment plan involves multiple treatment planning steps. For example, the process typically includes specifying target tissue structures and normal tissue structures in the treatment planning CT image, such as the GTV, the CTV, the internal target volume (ITV), the PTV, organs at risk (OAR), a planning organ at risk volume (PRV), and/or the like. In some embodiments, the process further includes steps such as target segmentation, OAR segmentation, plan optimization, and/or the like. Typically, the treatment plan is based on the treatment planning CT image that is generated in step 701, and includes one or more beam geometries for implementing the planned treatment and an optimized dose distribution for each beam geometry.

In step 703, implementation of a treatment fraction begins. Generally, a radiation therapy process includes multiple treatment fractions that are each performed by a radiation therapy system on a different clinical visit. For example, in some embodiments, each treatment fraction is performed on a different day. Thus, in the embodiment illustrated in FIG. 7, multiple iterations of steps 703-716 are performed in the course of completing a planned radiation therapy process.

For a particular treatment fraction, in step 703 a patient is precisely positioned relative to the radiation therapy system at a treatment position. For example, in some embodiments, when the patient is disposed at the treatment position, an isocenter of the radiation therapy system coincides with the target volume associated with the patient, such as target volume 610. In some embodiments, the patient is precisely positioned at the treatment position via a couch of the radiation therapy system, such as couch 307, and/or via one or more patient-monitoring optical sensors, such as patient-monitoring optical sensors 309. In some embodiments, the patient is positioned via external markings on the body of the patient. Alternatively or additionally, in some embodiments, the patient is positioned based on X-ray imaging performed in step 703.

In step 704, breathing cycle data is collected for the patient while the patient is disposed at the treatment position. For example, in some embodiments, the radiation therapy system performing the current treatment fraction receives a breathing signal that indicates an inspiration level of the patient. In some embodiments, a breath-hold curve is generated based on the breathing signal. In such embodiments, the breath-hold curve can indicate whether the inspiration level that the patient can maintain at the time of the current treatment fraction meets or exceeds the predetermined threshold inspiration level, such as predetermined threshold level 120.

In step 705, the radiation therapy system performing the current treatment fraction determines whether the patient can maintain an inspiration level that is equal to or greater than predetermined threshold level 120. In some embodiments, the determination is made based on the breath-hold curve and/or other breathing cycle data collected in step 704. For example, in some embodiments, breathing cycle data collected in step 704 is compared to predetermined threshold level 120. When the patient can maintain such an inspiration level, radiation therapy process 700 proceeds to step 710; when the patient cannot maintain such an inspiration level, radiation therapy process 700 proceeds to step 711.

In step 710, a normal treatment fraction from the treatment plan is performed. In some embodiments, performance of the normal treatment fraction includes applying beam parameters and dose distributions determined for the patient based on the treatment plan generated for the patient in step 702. In some embodiments, performance of the normal fraction includes additional X-ray imaging of the patient while the patient is disposed at the treatment position and modification of one or more beam parameters and/or dose distributions based on the additional X-ray imaging. For example, changes in patient anatomy that have occurred since the treatment planning CT scan was performed in step 701 can be compensated for at this time. Alternatively, in some embodiments, performance of the normal fraction does not include additional X-ray imaging of the patient. In either case, in step 710, the current treatment fraction is performed without modifications to the treatment plan that are based on a different inspiration level than maintained by the patient when the treatment planning CT scan was performed. After completion of the treatment fraction, radiation therapy process 700 proceeds to step 716.

In some embodiments, the normal treatment fraction is performed over a single rotational arc of a gantry of the radiation therapy system. Alternatively, in some embodiments, the normal treatment fraction is performed over multiple rotational arcs of a gantry of a radiation therapy system. Alternatively, in some embodiments, the normal treatment fraction is performed over a fraction of a rotational arc of a gantry of a radiation therapy system or over multiple separate fractions of a rotational arc of the gantry. Alternatively, in some embodiments, the normal treatment fraction is performed in a static-gantry radiation therapy process, such as an IMRT or a 3D-conformal radiation therapy process.

In step 711, the radiation system performing the current treatment fraction determines the current fraction inspiration threshold, such as current fraction inspiration threshold 220, based on the breathing signal received in step 704.

In step 712, the radiation therapy system performing the current treatment fraction acquires projection images of the patient. For example, in some embodiments, the projection images are acquired via a CBCT scan of the patient. In step 712, the projection images of the patient are acquired while the patient remains disposed in the treatment position set up in step 703. Further, the projection images of the patient are acquired while the patient maintains the current fraction inspiration threshold determined in step 711.

In step 713, a synthetic CT image that includes the target volume is generated. The synthetic CT image is based on the treatment planning digital volume associated with the radiation therapy process, such as the treatment planning CT image generated in step 701. The synthetic CT image is further based on the projection images of the patient acquired in step 712. In some embodiments, the synthetic CT image is generated by deformably registering image data within the treatment planning digital volume onto corresponding image data associated with the set of projection images. For example, in some embodiments, a digital volume is generated based on the set of projection images of the patient acquired in step 712, and this digital volume captures the current anatomy of the patient when maintaining the current fraction inspiration threshold. In such embodiments, image data within the treatment planning digital volume is deformably registered onto corresponding image data included in the digital volume that captures the current anatomy of the patient when maintaining an inspiration level that meets or exceeds the current fraction inspiration threshold. Thus, in such embodiments, in step 713 the synthetic CT image is generated by modifying the treatment planning digital volume based on the anatomy of the patient when maintaining an inspiration level that meets or exceeds the current fraction inspiration threshold but does not meet or exceed predetermined threshold level 120.

In step 714, a modified treatment fraction is generated based on the synthetic CT image generated in step 713 and the treatment plan generated in step 702. For example, in some embodiments, generating the modified treatment fraction includes detecting anatomical structures within the synthetic CT image. In such embodiments, such anatomical structures include one or more of the GTV, the CTV, the ITV, the PTV, one or more organs at risk (OAR), a PRV, and/or the like. In some embodiments, a conventional autosegmentation process or autosegmentation software application is employed to detect one or more such anatomical structures. Alternatively or additionally, in some embodiments, an artificial intelligence algorithm is employed to detect one or more such anatomical structures.

In some embodiments, generating the modified treatment fraction includes determining one or more treatment beam parameters for the modified treatment fraction based on the anatomical structures detected within the treatment planning digital volume. Thus, in such embodiments, one or more treatment beam parameters associated with the treatment plan generated in step 702 are modified based on the current anatomy of the patient when maintaining the current fraction inspiration threshold.

In step 715, the radiation therapy system performs the modified treatment fraction while the patient remains in the treatment position and maintains an inspiration level that meets or exceeds the current fraction inspiration threshold, such as current fraction inspiration threshold 220. Similar to step 710, in step 715, the modified treatment fraction can be performed over a single rotational arc, multiple rotational arcs, a fraction of a rotational arc, multiple separate fractions of a rotational arc of a gantry of the radiation therapy system, or via multiple static IMRT fields.

In step 716, the radiation therapy system performing the current treatment fraction determines whether any treatment fractions remain to be performed. If yes, radiation therapy process 700 returns to step 703; if no, radiation therapy process 700 proceeds to step 720 and terminates.

According to various embodiments, a modified treatment fraction is generated and implemented for each treatment fraction of a treatment plan. In such embodiments, for each treatment fraction, a modified treatment fraction is generated based on the inspiration level that can be maintained by the patient on the day of the treatment fraction. One such embodiment is described below in conjunction with FIG. 8.

Figure 8:
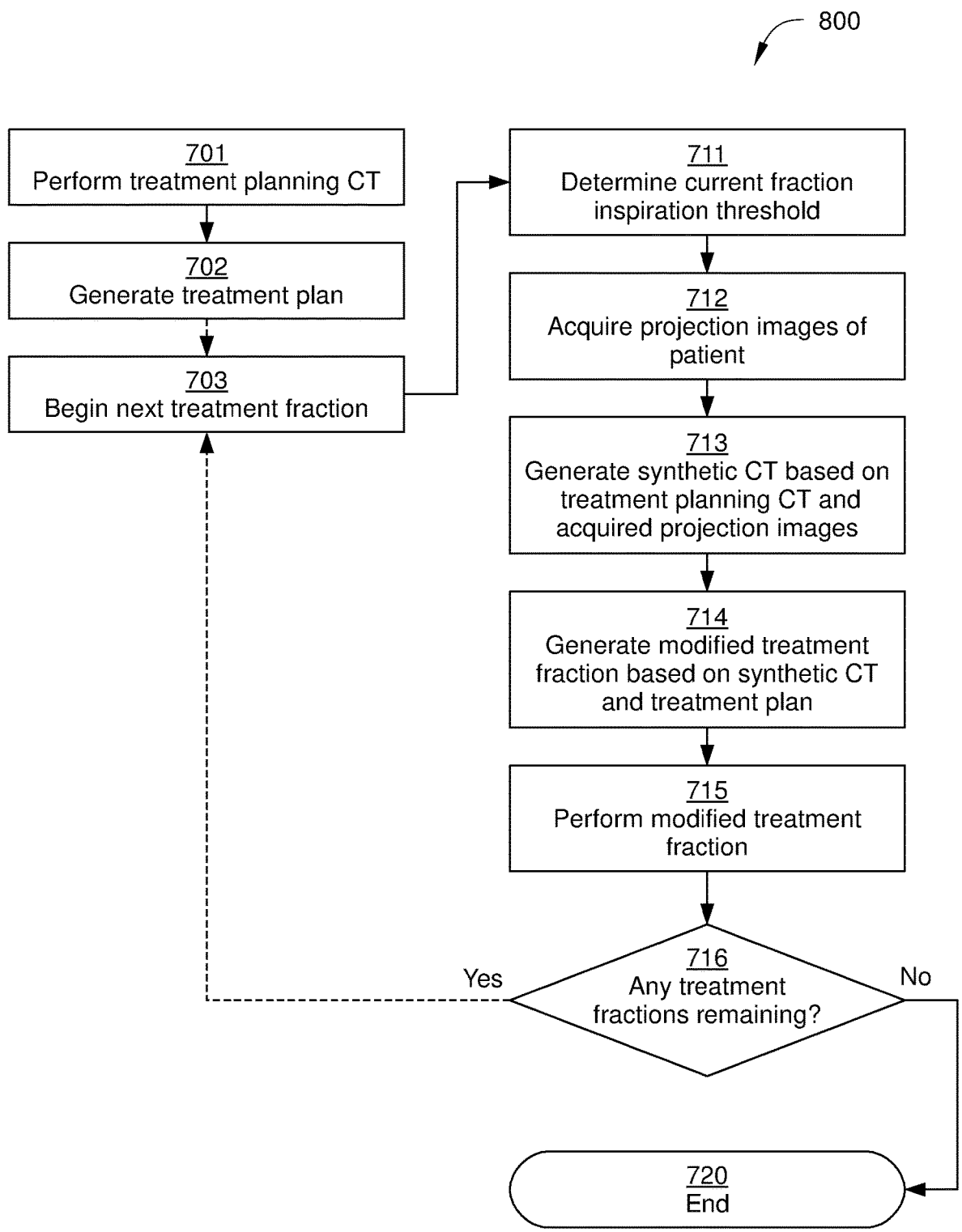
FIG. 8 sets forth a flowchart of a radiation therapy process, according to one or more embodiments.

FIG. 8 sets forth a flowchart of a radiation therapy process 800, according to one or more embodiments. Radiation therapy process 800 may include one or more operations, functions, or actions as illustrated by one or more of blocks 701-720. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although radiation therapy process 800 is described in conjunction with the systems of FIGS.

1-6, persons skilled in the art will understand that any suitably configured radiation therapy system is within the scope of the present embodiments.

As shown, radiation therapy process 800 is substantially similar to radiation therapy process 700 of FIG. 7, except that steps 704, 705, and 710 of radiation therapy process 700 are not included in radiation therapy process 800. Instead, the same process flow is performed for each treatment fraction, and there is no check to confirm that the patient can maintain an inspiration level that is equal to or greater than predetermined threshold level 120. In FIG. 8, each of blocks 701-720 of radiation therapy process 800 is substantially the same as a corresponding step in radiation therapy process 700, and therefore is numbered accordingly.

Example Computing Device

Figure 9:
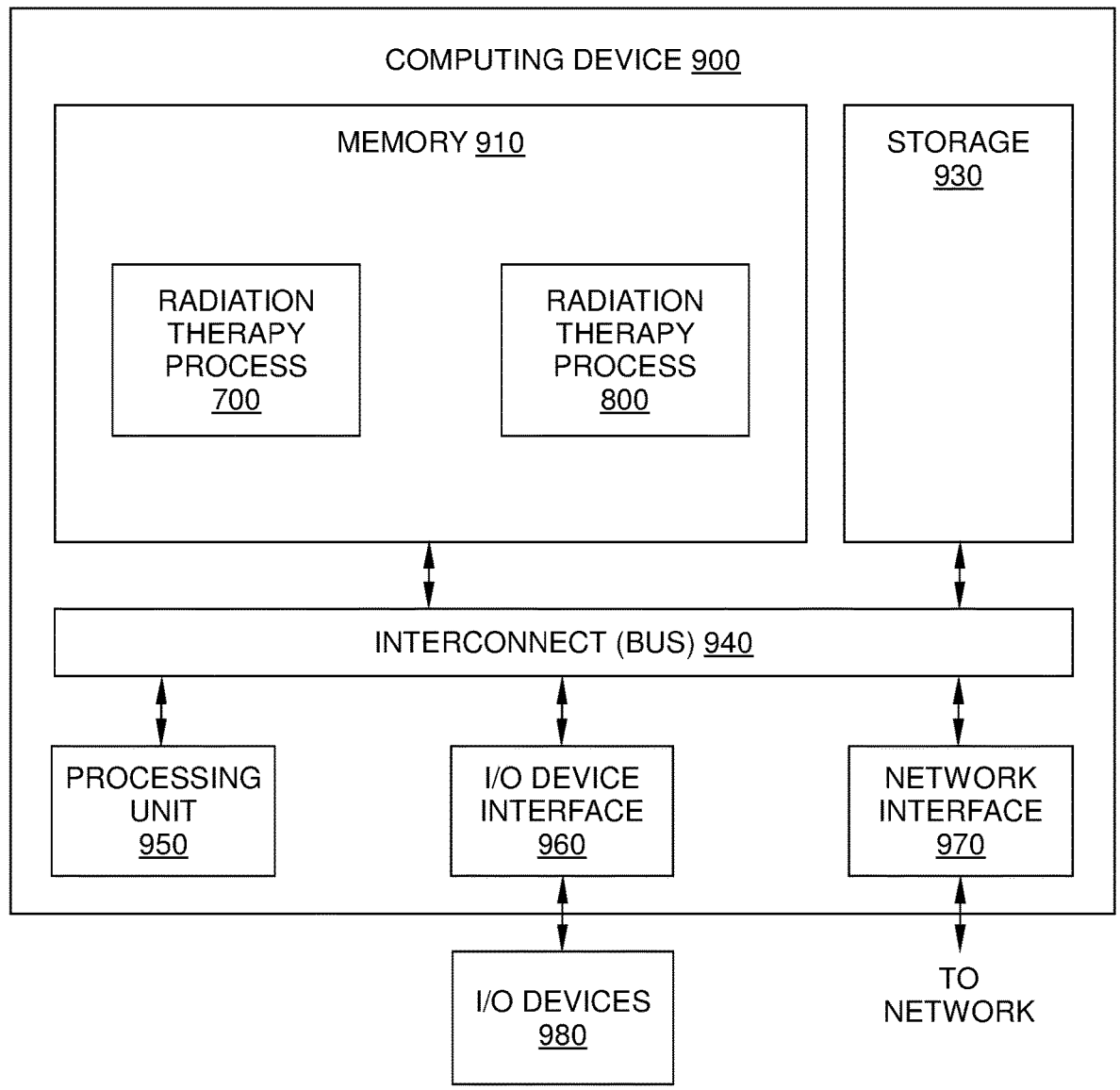
FIG. 9 is an illustration of a computing device configured to perform various embodiments of the present disclosure.

FIG. 9 is an illustration of computing device 900 configured to perform various embodiments of the present disclosure. For example, in some embodiments, computing device 900 can be implemented as image acquisition and treatment control computer 306 and/or remote control console 310 in FIG. 4. Computing device 900 may be a desktop computer, a laptop computer, a smart phone, or any other type of computing device suitable for practicing one or more embodiments of the present disclosure. In operation, computing device 900 is configured to execute instructions associated with radiation therapy process 700 and/or radiation therapy process 800, as described herein. It is noted that the computing device described herein is illustrative and that any other technically feasible configurations fall within the scope of the present disclosure.

As shown, computing device 900 includes, without limitation, an interconnect (bus) 940 that connects a processing unit 950, an input/output (I/O) device interface 960 coupled to input/output (I/O) devices 980, memory 910, a storage 930, and a network interface 970. Processing unit 950 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 950 may be any technically feasible hardware unit capable of processing data and/or executing software applications, including radiation therapy process 700 and/or radiation therapy process 800.

I/O devices 980 may include devices capable of providing input, such as a keyboard, a mouse, a touch-sensitive screen, and so forth, as well as devices capable of providing output, such as a display device and the like. Additionally, I/O devices 980 may include devices capable of both receiving input and providing output, such as a touchscreen, a universal serial bus (USB) port, and so forth. I/O devices 980 may be configured to receive various types of input from an end-user of computing device 900, and to also provide various types of output to the end-user of computing device 900, such as displayed digital images or digital videos. In some embodiments, one or more of I/O devices 980 are configured to couple computing device 900 to a network.

Memory 910 may include a random access memory (RAM) module, a flash memory unit, or any other type of memory unit or combination thereof. Processing unit 950, I/O device interface 960, and network interface 970 are configured to read data from and write data to memory 910. Memory 910 includes various software programs that can be executed by processor 950 and application data associated with said software programs, including radiation therapy process 700 and/or radiation therapy process 800.

Example Computer Program Product

Figure 10:
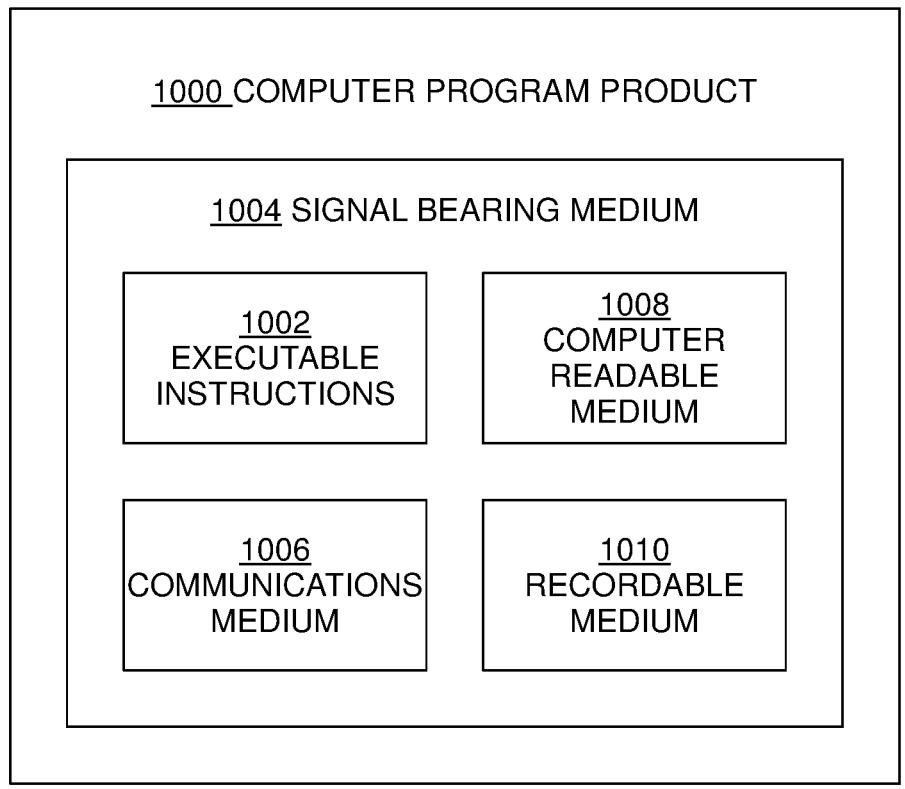
FIG. 10 is a block diagram of an illustrative embodiment of a computer program product for implementing one or more embodiments of the present disclosure.

FIG. 10 is a block diagram of an illustrative embodiment of a computer program product 1000 for implementing a method for radiation therapy, according to one or more embodiments of the present disclosure. Computer program product 1000 may include a signal bearing medium 1004. Signal bearing medium 1004 may include one or more sets of executable instructions 1002 that, when executed by, for example, a processor of a computing device, may provide at least the functionality described above with respect to FIGS. 1-9.

In some implementations, signal bearing medium 1004 may encompass a non-transitory computer readable medium 1008, such as, but not limited to, a hard disk drive, a Compact Disc (CD), a Digital Video Disk (DVD), a digital tape, memory, etc. In some implementations, signal bearing medium 1004 may encompass a recordable medium 1010, such as, but not limited to, memory, read/write (R/W) CDs, R/W DVDs, etc. In some implementations, signal bearing medium 1004 may encompass a communications medium 1006, such as, but not limited to, a digital and/or an analog communication medium (e.g., a fiber optic cable, a waveguide, a wired communications link, a wireless communication link, etc.). Computer program product 1000 may be recorded on non-transitory computer readable medium 1008 or another similar recordable medium 1010.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method of performing a radiation therapy process, the method comprising:
    while a patient is disposed in a first position for a first treatment fraction of the radiation therapy process and maintains a first inspiration level, acquiring a first set of projection images of a target volume associated with the patient;
    based on a treatment planning digital volume associated with the radiation therapy process and the first set of projection images of the target volume associated with the patient, generating a synthetic digital volume that includes the target volume;
    based on a treatment plan associated with the treatment planning digital volume and on the synthetic digital volume, generating a second modified treatment fraction of the radiation therapy process that is based on the first treatment fraction of the radiation therapy process; and
    while the patient remains in the first position for the first treatment fraction of the radiation therapy process and maintains at least the first inspiration level, performing the second modified treatment fraction of the radiation therapy process.

2. The computer-implemented method of claim 1, wherein the treatment planning digital volume is based on a second set of projection images from a treatment planning CT scan of the target volume associated with the patient.

3. The computer-implemented method of claim 1, wherein acquiring the first set of projection images of the target volume associated with the patient comprises performing a cone-beam computed tomography scan of the target volume.

4. The computer-implemented method of claim 1, further comprising, prior to acquiring the first set of projection images of the target volume associated with the patient, determining that the patient cannot maintain an inspiration level that meets or exceeds a predetermined threshold.

5. The computer-implemented method of claim 4, wherein determining that the patient cannot maintain the inspiration level that meets or exceeds the predetermined threshold comprises receiving a breathing signal that indicates an inspiration level of the patient.

6. The computer-implemented method of claim 4, wherein determining that the patient cannot maintain the inspiration level that meets or exceeds the predetermined threshold is performed while the patient is disposed in the first position.

7. The computer-implemented method of claim 1, wherein generating the synthetic digital volume comprises deformably registering image data within the treatment planning digital volume onto corresponding image data associated with the first set of projection images of the target volume associated with the patient.

8. The computer-implemented method of claim 7, wherein generating the second modified treatment fraction comprises detecting anatomical structures within the treatment planning digital volume after the image data within the treatment planning digital volume are deformably registered onto the corresponding image data associated with the first set of projection images of the target volume associated with the patient.

9. The computer-implemented method of claim 8, wherein generating the second modified treatment fraction further comprises determining one or more treatment beam parameters for the second modified treatment fraction based on the anatomical structures detected within the treatment planning digital volume associated with the radiation therapy process.

10. The computer-implemented method of claim 1, further comprising, prior to acquiring the first set of projection images of the target volume associated with the patient, determining that the first inspiration level is less than a predetermined threshold level associated with the treatment plan.

11. The computer-implemented method of claim 10, wherein the treatment plan is based on the patient maintaining an inspiration level that is equal to or greater than the predetermined threshold level.

12. The computer-implemented method of claim 1, further comprising, prior to performing the second modified treatment fraction, determining that the patient maintains at least the first inspiration level.

13. The computer-implemented method of claim 12, wherein determining that the patient maintains at least the first inspiration level comprises receiving a breathing signal that indicates a current inspiration level of the patient.

14. A system for performing treatment fractions of a radiation therapy process, the system comprising:
    an X-ray imager;
    a treatment-delivering X-ray source configured to direct treatment X-rays to a target volume of patient anatomy;
    an imaging X-ray source configured to direct imaging X-rays through the target volume and toward the X-ray imager; and
    a processor configured to:
        while a patient is disposed in a first position for a first treatment fraction of the radiation therapy process and maintains a first inspiration level, acquire a first set of projection images of a target volume associated with the patient;
        based on a treatment planning digital volume associated with the radiation therapy process and the first set of projection images of the target volume associated with the patient, generate a synthetic digital volume that includes the target volume;
        based on a treatment plan associated with the treatment planning digital volume and on the synthetic digital volume, generate a second modified treatment fraction of the radiation therapy process that is based on the first treatment fraction of the radiation therapy process; and
        while the patient remains in the first position for the first treatment fraction of the radiation therapy process and maintains at least the first inspiration level, cause the second modified treatment fraction of the radiation therapy process to be performed.

15. The system of claim 14, wherein the treatment planning digital volume is based on a second set of projection images of a treatment planning CT scan of the target volume.

16. The system of claim 14, wherein acquiring the first set of projection images of the target volume associated with the patient comprises performing a cone-beam computed tomography scan of the target volume.

17. The system of claim 14, further comprising, prior to acquiring the first set of projection images of the target volume associated with the patient, determining that the patient cannot maintain an inspiration level that meets or exceeds a predetermined threshold.

18. The system of claim 17, wherein determining that the patient cannot maintain the inspiration level that meets or exceeds the predetermined threshold comprises receiving a breathing signal that indicates a current inspiration level of the patient.

19. The system of claim 17, wherein determining that the patient cannot maintain the inspiration level that meets or exceeds the predetermined threshold is performed while the patient is disposed in the first position.

20. The system of claim 14, wherein generating the synthetic digital volume comprises deformably registering image data within the treatment planning digital volume onto corresponding image data associated with the first set of projection images of the target volume associated with the patient.

* * * * *